United States Patent
Lowry et al.

(10) Patent No.: US 10,219,688 B2
(45) Date of Patent: Mar. 5, 2019

(54) SYSTEM AND METHOD FOR THE SELECTION OF OPTICAL COHERENCE TOMOGRAPHY SLICES

(71) Applicant: The Charles Stark Draper Laboratory Inc., Cambridge, MA (US)

(72) Inventors: Nathan Lowry, Malden, MA (US); Peter Lommel, Andover, MA (US); Lei Hamilton, Lexington, MA (US); Rami Mangoubi, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/296,786

(22) Filed: Oct. 18, 2016

(65) Prior Publication Data

US 2017/0105616 A1    Apr. 20, 2017

Related U.S. Application Data

(60) Provisional application No. 62/243,438, filed on Oct. 19, 2015.

(51) Int. Cl.
*G06T 7/12* (2017.01)
*A61B 3/00* (2006.01)
*A61B 3/10* (2006.01)
*A61B 3/12* (2006.01)
*G06K 9/46* (2006.01)
(Continued)

(52) U.S. Cl.
CPC ............ *A61B 3/0025* (2013.01); *A61B 3/102* (2013.01); *A61B 3/1025* (2013.01); *A61B 3/1225* (2013.01); *G06K 9/4604* (2013.01); *G06K 9/6267* (2013.01); *G06T 7/0012* (2013.01); *G06T 7/12* (2017.01);
(Continued)

(58) Field of Classification Search
CPC ................................ G06T 7/12; G06K 9/4604
USPC ......................................................... 382/131
See application file for complete search history.

(56) References Cited

U.S. PATENT DOCUMENTS 8,879,813 B1    11/2014  Solanki et al.
2007/0109499 A1*  5/2007  Yan ........................... A61B 3/12
                                                                  351/221
(Continued)

FOREIGN PATENT DOCUMENTS

WO    WO-2010/117386    10/2010
WO    WO-2010/140476    12/2010

OTHER PUBLICATIONS

International Search Report and Written Opinion for PCT/US2016/057520 dated Jan. 19, 2017.

*Primary Examiner* — Raj Chakraborty
(74) *Attorney, Agent, or Firm* — Christopher J. McKenna; Foley & Lardner LLP (57) ABSTRACT

The present disclosure describes systems and methods to select fovea containing optical coherence tomography (OCT) images. The systems and methods described herein receive a plurality of OCT images. The portion of the OCT images are selected for further processing, where a line tracing the border between the retina and non-retina tissue is generated. A difference of the line is generated. Candidate OCT images are then generated responsive to the generated difference line. The lowest point among each difference lines generated for each of the OCT images is identified, and the OCT image to which the lowest point corresponds is identified as the fovea containing OCT image.

20 Claims, 7 Drawing Sheets

(51) Int. Cl.
*G06K 9/62* (2006.01)
*G06T 7/00* (2017.01)

(52) U.S. Cl.
CPC .............. *G06T 2207/10101* (2013.01); *G06T 2207/20076* (2013.01); *G06T 2207/30041* (2013.01)

(56) References Cited

U.S. PATENT DOCUMENTS

| | | | | |
|---|---|---|---|---|
| 2014/0003739 | A1* | 1/2014 | Basavaraja | H04N 19/172 382/284 |
| 2014/0268040 | A1* | 9/2014 | Mujat | A61B 3/102 351/206 |
| 2015/0002816 | A1* | 1/2015 | Kowal | A61B 3/156 351/207 |
| 2015/0085253 | A1* | 3/2015 | Walsh | A61B 3/102 351/208 |
| 2015/0206354 | A1* | 7/2015 | Shibuhisa | H04N 5/23219 348/46 |

* cited by examiner

SYSTEM AND METHOD FOR THE SELECTION OF OPTICAL COHERENCE TOMOGRAPHY SLICES

CROSS-REFERENCE TO RELATED APPLICATIONS

This application claims the benefit of and priority to U.S. Provisional Patent Application No. 62/243,438 filed on Oct. 19, 2015, which is herein incorporated by reference in its entirety.

BACKGROUND OF THE DISCLOSURE

Optical Coherence Tomography (OCT) is an optical imaging technology that can generate non-invasive, real time, high-resolution cross sectional images of tissue structures. In many implementations, the images captured by OCT device have a micrometer resolution.

OCT devices can generate cross-sectional images of a patient's retina—providing a view of the different retinal layers. The cross-sectional images (also referred to as slices) can be useful in the diagnosis of retinal diseases. In some cases, cross-sectional images near predetermined ocular structures, such as the fovea, can be the most important when making clinical decisions based on the cross-sectional images. The fovea can be important because the fovea includes a concentration of cones and rods.

SUMMARY OF THE DISCLOSURE

According to one aspect of the disclosure, a method for selecting clinically relevant optical coherence tomography (OCT) images includes receiving a plurality of OCT images. For each of the plurality of OCT images the method includes identifying an outline of a retina tissue surface in the respective OCT image and then calculating a derivative of the outline. The method can also include identifying one of the plurality of OCT images containing a fovea. The image containing the fovea can be identified in the OCT image as the OCT image having the derivative a greatest magnitude.

In some implementations, the method includes discarding a portion of the plurality of OCT images prior to identifying the line outlining the retina tissue. In some implementations, the derivative of the line is a second derivative of the line. In some implementations, the method includes determining if the derivative of the line crosses a predetermined threshold.

In some implementations, the method includes receiving a prior probability distribution for the line outlining the retina tissue surface in the respective OCT image. The method also includes calculating a probability that each point of the line outlining the retina tissue surface corresponds to a fovea. The probability is calculated using Bayes' rule.

In some implementations, the method also includes identifying the outline of the retina tissue surface in the respective OCT image using a Bayesian level set algorithm. The Bayesian level set algorithm can be used to classify each pixel of the respective OCT image as a retina or a non-retina pixel. The outline of the retina tissue surface can be substantially the shortest path between the retina and the non-retina pixels. In some implementations, a smoothing filter is applied to the derivative of the outline of the retina tissue surface.

According to another aspect of the disclosure, a system for selecting clinically relevant OCT images includes a memory and one or more processors that are configured to execute instructions stored in the memory. Execution of the instructions cause the one or more processors to receive a plurality of OCT images. For each of the plurality of OCT images the one or more processors identify an outline of a retina tissue surface in the respective OCT image. The one or more processor can then calculate a derivative of the line. The one or more processors also identify one of the plurality of OCT images containing a fovea. The image containing the fovea can be identified in the OCT image as the OCT image having the derivative a greatest magnitude.

In some implementations, the instructions cause the one or more processors to discard a portion of the plurality of OCT images prior to identifying the line outlining the retina tissue. In some implementations, the derivative of the line is a second derivative of the line. In some implementations, the instructions cause the one or more processors to determine if the derivative of the line crosses a predetermined threshold.

In some implementations, the instructions cause the one or more processors to receive a prior probability distribution for the line outlining the retina tissue surface in the respective OCT image. The instructions cause the one or more processors to calculate a probability that each point of the line outlining the retina tissue surface corresponds to a fovea. The probability is calculated using Bayes' rule.

In some implementations, the instructions cause the one or more processors to identify the outline of the retina tissue surface in the respective OCT image using a Bayesian level set algorithm to classify each pixel of the respective OCT image as a retina or a non-retina pixel. The outline of the retina tissue surface can be substantially the shortest path between the retina and the non-retina pixels. The instructions also cause the one or more processors to apply a smoothing filter to the derivative of the outline of the retina tissue surface.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods described herein automatically select near-fovea OCT image slices from a plurality of OCT images across the retina. Near-fovea OCT images can be used in the diagnosis of ocular diseases and the assessment of the retina. The selected slices can be segmented and then features can be extracted from the selected slices. The features and slices can be used for diagnosis, procedure and drug effect outcome prediction, and post-procedure efficacy analysis.

Figure 1:
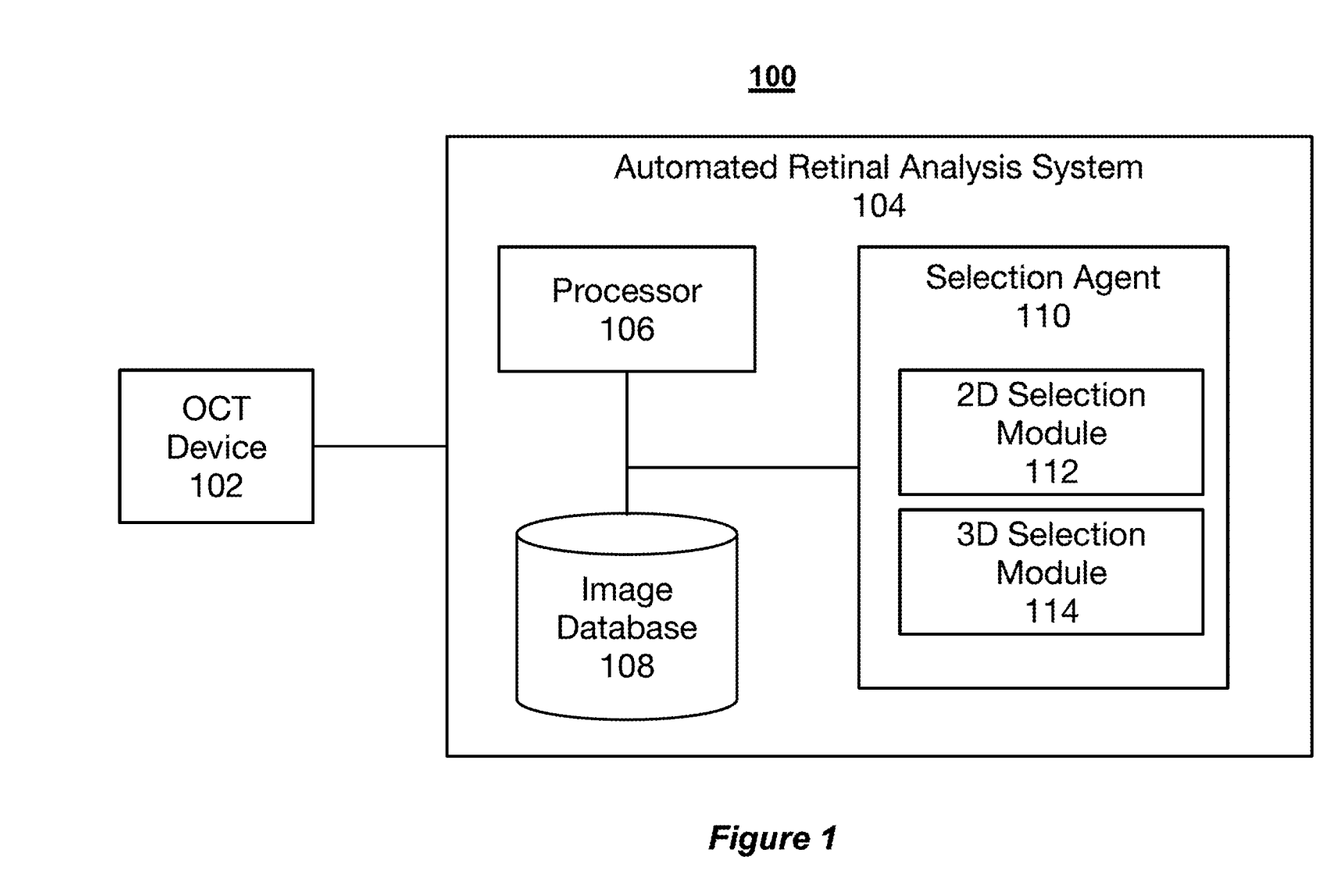
FIG. 1 illustrates an example system for selecting near-fovea and fovea containing OCT images.

FIG. 1 illustrates an example system 100 for selecting near-fovea and fovea containing OCT images. The system 100 includes an OCT device 102 that is coupled to an automated retinal analysis system (ARAS) 104. The ARAS 104 includes a processor 106 and an image database 108. The ARAS 104 also includes a selection agent 110, which includes a 2D selection module 112 and/or a 3D selection module 114.

The OCT device 102 of the system 100 includes one or more OCT devices 102 that generate the OCT images. The OCT device 102 is a device configured to measure the thickness of tissue, such as the retinal thickness and the retinal nerve fiber layer thickness. The OCT device 118 can be any type of OCT device that generates an OCT image. In some implementations, the OCT device 102 is located remotely from the ARAS 104. For example, images are captured by the OCT device 102 and transferred to the ARAS 104 over a network, such as the internet. In other implementations, ARAS 104 is located local to the OCT device 102 or may be a component of the OCT device 102. In general, the OCT device 102 generates a plurality of A-scans across the retina or a region of interest. Each A-scan measures a time-delay of light reflected from a specific point location on the retina. Neighboring A-scans are laterally combined to create cross-sectional images of the retina. The laterally combined A-scans are referred to as B-scan images (or generally, OCT images or OCT slices). A total OCT scan includes generating a plurality of A-scans along both an x axis and a y axis over a region of interest. The A-scans along one of the axes are laterally combined to form a plurality of cross-sectional OCT slices. For example, and assuming a 256×256 grid of A-scans, the A-scans at location (1, y) are laterally combined to form a first B-scan, the A-scans at location (2, y) are laterally combined to form a second B-scan, and so forth until the A-scans at location (256, y) are laterally combined to form a $256^{th}$ B-scan. The A-scans can be laterally combined along the x or y axis.

The ARAS 104 of the system 100 is configured to automatically select near- and through-fovea OCT images (collectively referred to as near-fovea OCT images). The near-fovea OCT images can be of higher clinical relevance than compared to OCT images not near the fovea. Accordingly, the selection of near-fovea OCT images are selected prior to making diagnosis or other clinical judgments. The methods described herein are executed by the processor 106 of the ARAS 104. In some implementations, the processor 106 of the ARAS 104 is a processor of a general purpose computer executing software. In other implementations, the functions performed by the ARAS 104 are performed by special purpose logic circuitry, such as a field programmable gate array of application specific integrated circuit.

The ARAS 104 includes an image database 108. The image database 108 is configured to store OCT images captured by the OCT device 102. The image database 108 also stores the OCT indications of which of the stored OCT images are near-fovea OCT images. For example, an array may be stored in association with a set of OCT images. Each bit of the array may be set to 0 except for the OCT images the ARAS 104 determines are near- or through-fovea OCT images. The image database 108 can be stored on any type of computer readable medium such a hard drive, solid state drive, or other forms of volatile or non-volatile memory. In some implementations, memory on which the image database 108 is stored also stores computer executable instructions that are executed by the processor 106 to perform the methods described herein.

The ARAS 104 also includes a selection agent 110 to select near-fovea OCT images. The selection agent 110 is described in greater detail in relation to FIGS. 2-6. Briefly, the selection agent 110 includes processor executable instructions executed by the processor 106 or special purpose logic circuits to identify near-fovea OCT images provided to the ARAS 104. The selection agent 110 includes a 2D selection module 112 and a 3D selection module 114. The 2D selection module 112 uses one or more 2D based algorithms to analyze the OCT images to locate near-fovea OCT images. The 3D selection module 114 uses one or more 3D based algorithms to analyze the OCT images to locate near- and through-fovea OCT images. In some implementations, the 2D selection module 112 alone is used to identify near- or through-fovea OCT images, in other implementations the 3D selection module 114 alone is used to identify near- or through-fovea OCT images, and in other implementations, the 2D selection module 112 and the 3D selection module 114 work together in a hybrid fashion to identify near- and through-fovea OCT images.

Figure 2:
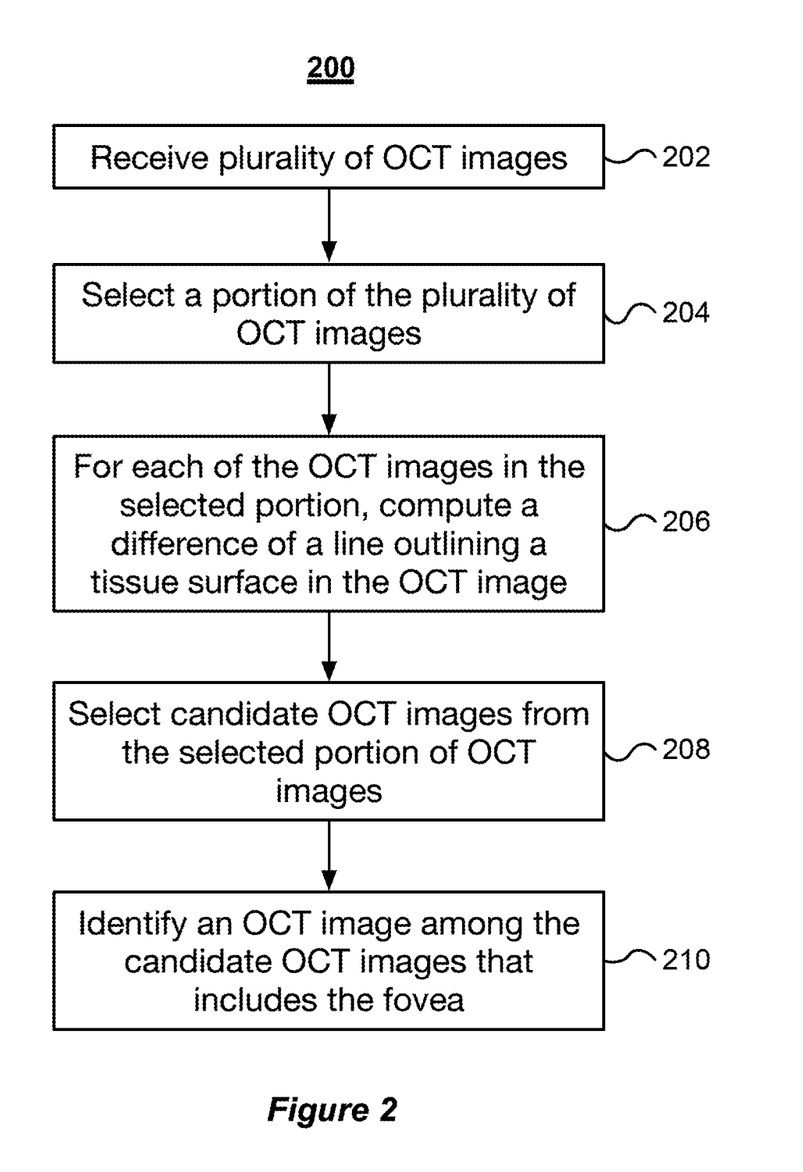
FIG. 2 illustrates a flow diagram of an example method for selecting near- and through-fovea OCT images using the system illustrated in FIG. 1.

FIG. 2 illustrates a flow diagram of an example method 200 for selecting near- and through-fovea OCT images. The method 200 includes receiving a plurality of OCT images (step 202). A portion of the received OCT images are selected for further review (step 204). For each of the selected OCT images, a difference between neighboring points of a line outlining the retina tissue surface is computed (step 206). Candidate OCT images are selected from the selected portion of OCT images responsive to the computed difference between neighboring points of a line outlining the retina tissue (step 208). One or more OCT images containing the fovea are then identified (step 210).

Figure 3A:
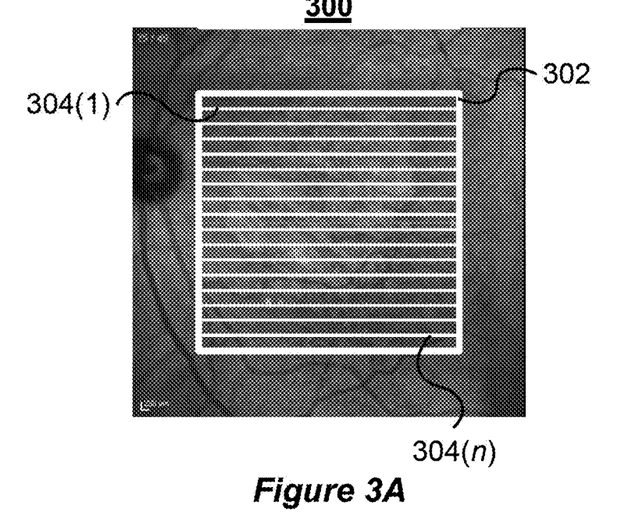
FIG. 3A illustrates an en face image of a retina captured using the system illustrated in FIG. 1.
Figure 3B:
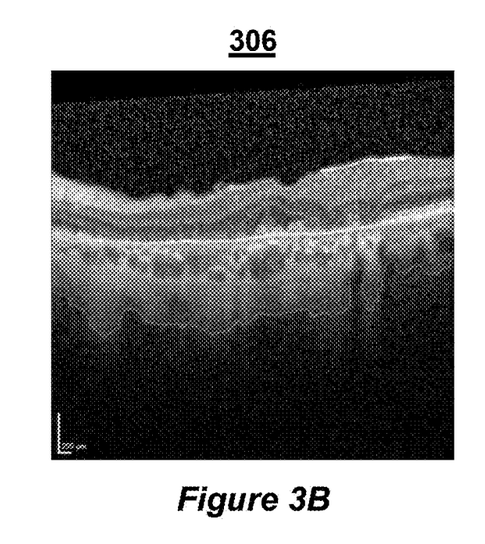
FIG. 3B illustrates an OCT image captured near the center of the en face image illustrated in FIG. 3A.

As set forth above, the method 200 includes receiving a plurality of OCT images (step 202). The plurality of OCT images is distributed across a region of interest. FIG. 3A illustrates an en face image 300 of a retina. A region of interest is designated by box 302. A plurality of OCT images is captured across the region of interest at locations 304(1)-304(n). Each of the OCT images is a cross-sectional image through the retina at a respective location 304. The plurality of OCT images captured at locations 304(1)-304(n) are referred to as a stack. FIG. 3B illustrates an OCT image 306 captured at a location 304 near the center of the region of interest illustrated in FIG. 3A.

Referring to FIG. 2, the method 200 also includes selecting a portion of the received OCT images for further review (step 204). Selecting only a portion of the OCT images to analyze may also be referred to as down-selecting the OCT images. In the down-selection process, OCT images that are unlikely to include the fovea, or other anatomical features of interest, are discarded. The process of down-selection, for example, reduces the number of OCT images analyzed from n to n-x. The OCT images are down selected because, in some implementations, it is assumed that the fovea is relatively centered within the en face image. This assumption allows the OCT images far from the center of the en face image to be discarded as there is a relatively high probability these OCT images do not include the fovea. For example, and also referring to FIG. 3A, if the OCT images are provided as a n image stack, wherein n is the number of OCT images, there is a high likelihood the fovea is located within one of the slices between slice n/2−(0.16)n and n/2+(0.16)n (i.e., the middle two-thirds). In this example, if the stack includes 49 slices (n=49), OCT images n=16 to 32 are selected as the portion of the OCT images for further processing, and the other OCT images are discarded or ignored. In some implementations, it is assumed the fovea is within about the central 10%, 15%, 20%, 25%, 30%, 35%, or about 40% of the stack.

Referring to FIG. 2, the example method 200 also includes, for each of the selected OCT images, computing a difference of neighboring points of a line outlining the retina tissue surface (step 206). The difference of neighboring points of a line outlining the retina tissue surface can generally be referred to as the difference or the first difference of a line outlining the retina tissue surface. In some implementations, the computed difference includes calculating the difference between neighboring points of the first difference line. The resulting line can be referred to as the second difference. In many OCT images, the fovea is located at a dip in a line tracing the top layer of retinal tissue. In some implementations, the fovea is located in a relatively high curvature region of the retinal tissue. Taking the first (and second) difference enables the dip in the retinal tissue boundary line that is indicative of the fovea to be detected in regions of high curvature. In some implementations, the first and second differences are smoothed with a moving average filter to reduce jitter present in the line tracing the top layer of retinal tissue.

Figure 4A:
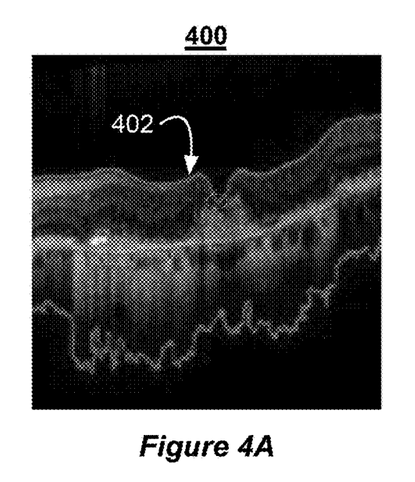
FIGS. 4A-4D illustrate finding the line outlining the retina tissue and calculating the derivative of the line.
Figure 4B:
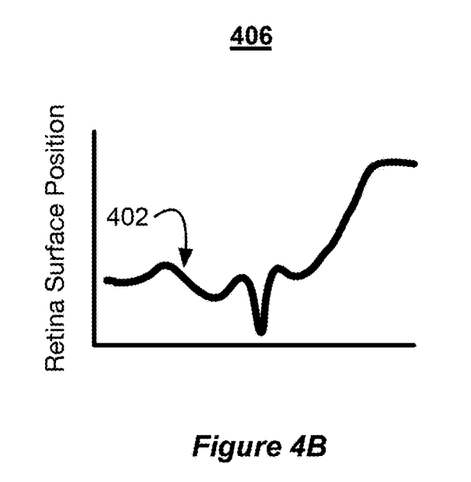
Figure 4C:
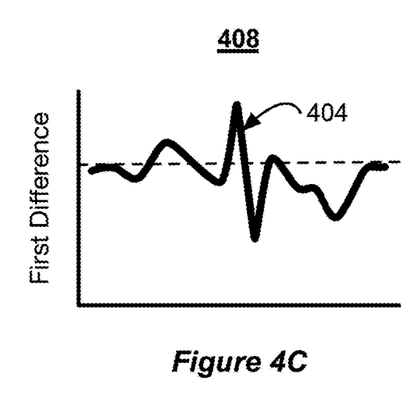
Figure 4D:
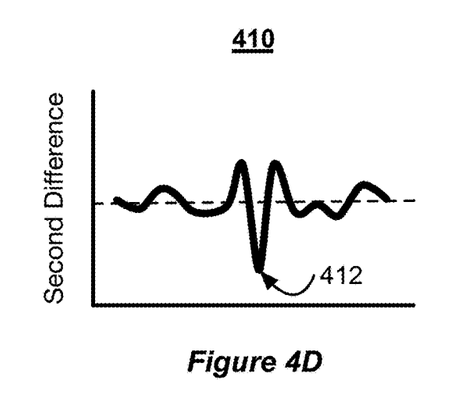

FIGS. 4A-4D illustrate the step 206 of finding the boundary line of the retina tissue and calculating a difference of the line. In some implementations, the boundary line of the retina tissue is also referred to as an outline of the retina tissue surface. FIG. 4A illustrates an OCT image 400. The location of the top layer of retinal tissue is identified, and the location of the pixels forming the top layer of tissue is captured to form a boundary 402. In some implementations, the boundary 402 is determined using a Bayesian level set algorithm to classify each pixel as a retina or a non-retina pixel. The boundary 402 can be the substantially shortest path through the uppermost pixels at the boundary between the retina and non-retina pixels. FIG. 4B illustrates a plot 406 of the boundary 402 from FIG. 4A. FIG. 4C illustrates a plot 408 of a first difference 404 between the y-values of adjacent points of the boundary 402. That is, the first difference 404 is the derivative of the boundary 402. In some implementations, the second difference is also calculated. FIG. 4D illustrates a plot 410 of a second difference 412 of the boundary 402. The second difference 412 is the second derivative of the boundary 402.

Referring to FIG. 2, the method 200 also includes selecting a portion of the OCT images as candidate OCT images (step 208). In some implementations, the candidate OCT image include the OCT images that have a 2nd difference between neighboring points of a line outlining the retina tissue that falls below a predetermined threshold. Valleys in the tissue, such as the fovea, have a 2nd difference line below 0. Natural undulations in the surface of the retinal tissue other than the fovea can also result in a 2nd difference line below 0. Setting a threshold substantially below 0 enables discrimination between OCT images that include natural undulations and OCT images that include the fovea. In some implementations, the threshold is manually set by a user of the system, and in other implementations, the threshold is automatically set. For example, the threshold can be set to be one standard deviation above the mean of the $2^{nd}$ difference line.

The method 200 also includes identifying an OCT image among the candidate OCT images that includes the fovea (step 210). Once the candidate slices are selected, the OCT image containing the lowest overall point in their respective $2^{nd}$ difference lines is identified as running through the center of the fovea. In some implementations, the remaining candidate OCT images are identified as near-fovea OCT images.

In some implementations, the method 200 can also include an optional error checking step that accounts for errors that may occur during the selection process. For example, in some implementations, the optical disc can be confused for the fovea. Selection of the optical disc can be avoided by discarding selections that find the fovea toward the extremes of the OCT image, because the fovea is typically relatively close to the middle of the OCT image, while the optical nerve is located toward one of the edges of the OCT image. In some implementations, the shape of the top layer of tissue is ambiguous, and there are a plurality of locations in the 2nd difference that are of relatively the same depth. In some of these implementations, the ambiguity can be corrected for by repeating the method 200, but with a new stack of OCT images that are orthogonal to the original set of OCT image. For example, the first iteration of the method 200 may receive OCT images that are generated through the lateral combination of A-scans along the x axis of the region of interest and the second iteration of the method 200 may receive OCT images generated through the lateral combination of A-scans along they axis of the region of interest.

Figure 5:
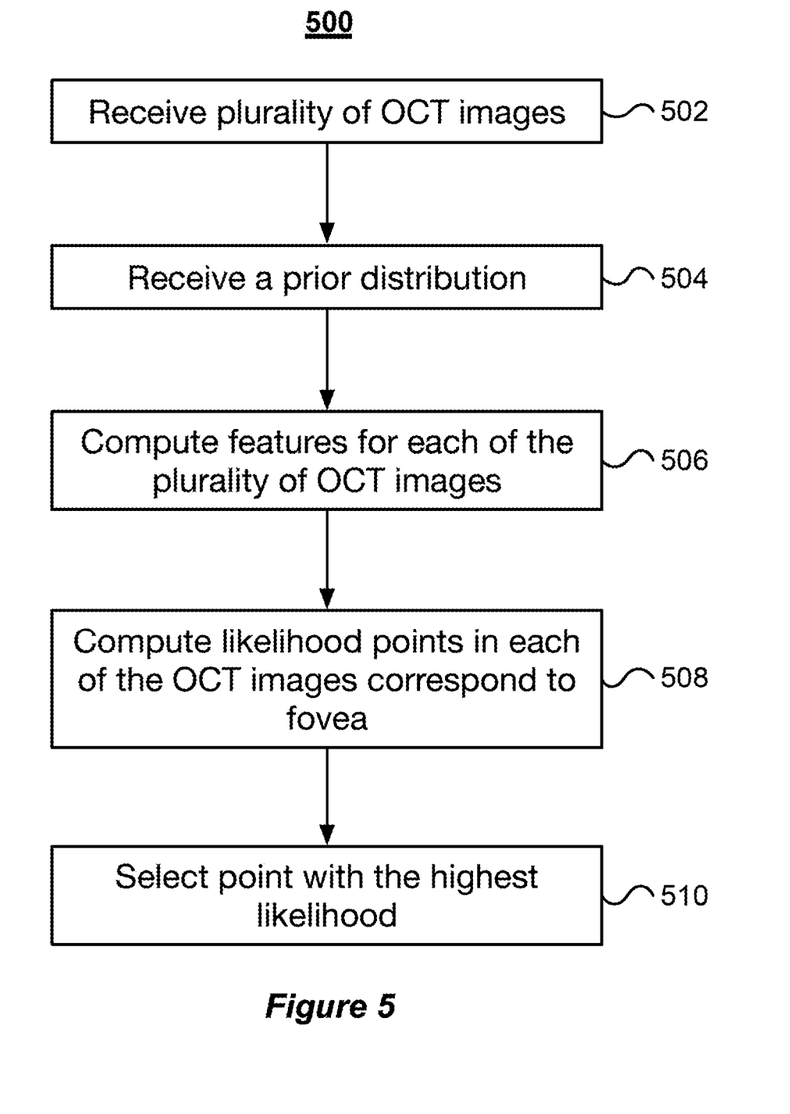
FIG. 5 illustrates another example method for identifying fovea containing OCT images using the system illustrated in FIG. 1.

FIG. 5 illustrates a flow diagram of another example method 500 for identifying fovea containing OCT images. The method 500 includes receiving a plurality of OCT images (step 502), and receiving a prior probability distribution for each of the OCT images (step 504). Features for each of the plurality of OCT images are then calculated (step 506). Bayes' rule is then applied to compute the likelihood that each point within each OCT image corresponds to the fovea (step 508). The point with the highest likelihood of being the fovea is then selected (step 510).

As set forth above, the method 500 includes receiving a plurality of OCT images (step 502). As described above in relation to FIGS. 2 and 3A, the plurality of OCT images is distributed over a region of interest. As in method 200, the plurality of OCT image is retrieved from an image database or received from another source. Next, the method 500 includes receiving a prior probability distribution (step 504). As described above in relation to FIGS. 2 and 4A, a line tracing the top of the retina tissue in each OCT image is generated. The prior probability distribution provides the probability that each point along the line tracing the top of the retina tissue corresponds to the fovea. In some implementations, the fovea is assumed to be near the center of the OCT image. In these implementations, the prior probability distribution has a standard deviation of 10% of the width of the OCT image. For example, the prior probability distribution accords the center pixel the highest probability of being the fovea with a standard deviation of 10% of the width of the OCT image.

Next, the method includes computing features for each of the plurality of OCT images (step 506). The features include depth, first differences, second differences for each point of a line that traces along the top layer of retina tissue in each OCT image, wavelet descriptors, Fourier transform coefficients, and features learned using machine learning. In some implementations, the features are also calculated for a second set of OCT images that run orthogonal to the original set of OCT images through the region of interest. The features calculated for the second set of OCT images help to disambiguate multiple fovea candidate OCT images.

Next, the likelihood that each point in the OCT image corresponds to the fovea is calculated (step 508). In some implementations, a marginal distribution and a distribution conditioned on the point containing the fovea for each feature is computed. Computing the feature distributions can include computing a histogram for each feature over all the top layer points, computing a histogram for each feature over the fovea points, and fitting a Gaussian distribution to each of the histograms. In some implementations, Bayes' rule is applied to compute the likelihood that each point within the top layer corresponds to the fovea, and then the point with the highest likelihood is selected as corresponding to the fovea. An indicator value F is calculated for each pixel (F=1 indicates that the pixel contains the fovea). Given that D is the depth of each pixel, $\Delta$ is the first difference at each pixel, $\Delta^2$ is the second difference at each pixel, and S is the slice number, the likelihood that each top layer pixel contains the fovea given the observations using Bayes' rule in the following form:

$$p(F \mid D, \Delta, \Delta^2, S) = \frac{p(D \mid F)p(\Delta \mid F)p(\Delta^2 \mid F)p(S \mid F)p(F)}{p(\Delta)p(\Delta^2)p(S)}$$

The method 500 concludes by selecting the OCT image that includes the point with the highest likelihood to be the fovea (step 510). Referencing the above equation, the OCT image that includes the pixel with the highest $P(F|D,\Delta,\Delta^2,S)$ is the OCT image selected as containing the fovea.

Figure 6:
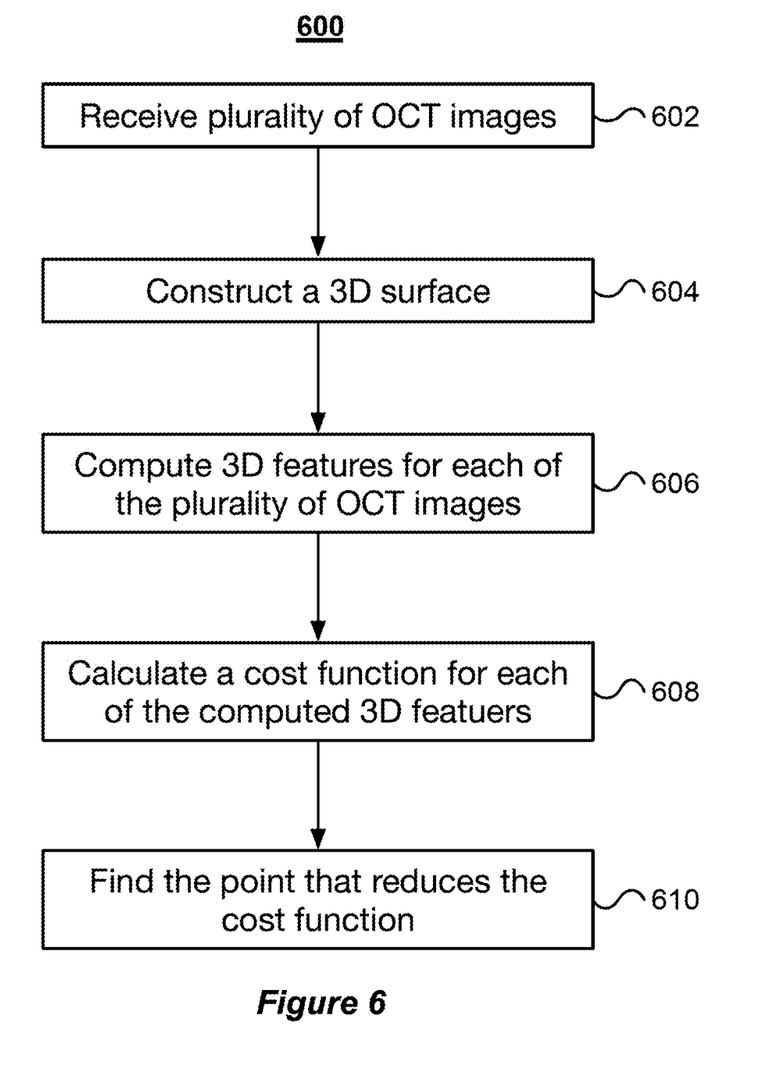
FIG. 6 illustrates a flow diagram of an example method for selecting fovea containing OCT images using a 3D surface and using the system illustrated in FIG. 1.

In some implementations, fovea slices are located by generating a 3D surface of the retina. FIG. 6 illustrates a flow diagram of an example method 600 for selecting fovea containing OCT images using a 3D surface. The method includes receiving a plurality of OCT images (step 602), and then constructing a 3D surface from the plurality of OCT images (step 604). Then, 3D features for each of the OCT images are computed (step 606). A cost function is then calculated over each of the computed 3D features (step 608). An optimization algorithm is applied to find the point which reduces the cost function and returns the function and its corresponding slice (step 610).

Figure 7:
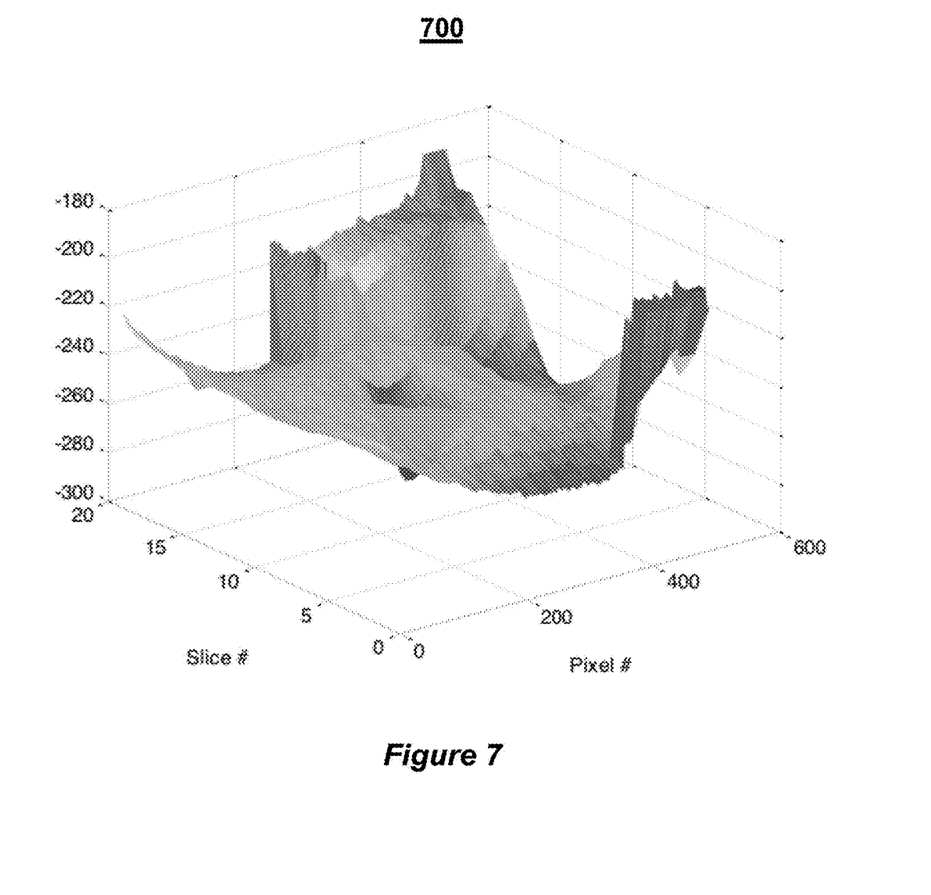
FIG. 7 illustrates an example 3D structure generated during the method illustrated in FIG. 6.

As set forth above, the method 600 includes receiving a plurality of OCT images (step 602), and then constructing a 3D surface (step 604). Once the plurality of OCT images are received by the selection agent as discussed above in relation to FIGS. 1, 2, and 5, the 3D surface is constructed. In some implementations, the inner limiting membrane (ILM) is identified in each of the OCT images. The location of the ILM in each of the OCT images is extracted and used to generate the 3D structure. For example, each of the OCT images are laterally combined to create a 3D volume that includes the retina tissue. The location of the ILM from the individual OCT images is used to form a 3D mesh through the 3D volume that defines the top layer of retina tissue. FIG. 7 illustrates an example 3D structure 700. The structure 700 is generated from twenty OCT images. The twenty line segments that define the ILM within each OCT image are combined to generate the 3D structure 700.

Referring to FIG. 6, the method 600 also includes calculating 3D features for the 3D surface (step 606). The 3D features can include calculating at least one of a surface depth, slope (gradients), a curvature (Laplacian), wavelet descriptors, Fourier transform coefficients, and features learned using machine learning for each of the points on the surface of the 3D structure. In some implementations, the features are calculated only for points near the center of the 3D structure.

The method 600 also includes calculating a cost function for each of the 3D features (step 608). Calculating the cost function can include minimizing the negative log of the likelihood that each pixel is the fovea using Bayesian inference. The Bayesian inference can be calculated using empirical estimation of the marginal likelihood of each feature and the likelihood of each feature conditioned on the fovea being contained in the pixel corresponding to the feature.

Next, the method 600 includes determining the point that reduces the cost function (step 610). An optimization algorithm can be applied to find the point which reduces the cost function. For example, a likelihood that each point includes the fovea can be defined by finding the maximum likelihood ILM point by calculating a gradient descent of the negative log likelihood. The likelihood can be provided by:

$$\mathrm{argmin}(p(D|F)p(\Delta/F)p(\Delta^2|F)p(S|F)P(F))$$

In some implementations, the fovea containing OCT images are selected using both the above described 2D algorithms (from method 200 and method 500) and the 3D algorithms (from method 600). These methods are referred to as hybrid methods. For example, in one hybrid example, one or more 2D features of the line tracing the top layer of the retina tissue in each of the OCT images is calculated (as described in relation to FIG. 5) and one or more 3D features of the 3D structure is calculated (as described in relation to FIG. 6). As described in relation to FIG. 5, the calculated 2D features and 3D features can be analyzed by applying Bayes' rule to compute the likelihood that each point corresponds to the fovea and a posteriori estimate can be made to select the OCT image containing the fovea.

In another example hybrid method, one or more 2D features of the line tracing the top layer of the retina tissue in each of the OCT images is calculated (as described in relation to FIG. 5) and one or more 3D features of the 3D structure is calculated (as described in relation to FIG. 5). The calculated features can then be fed into a cost function, as described in relation to FIG. 6.

The disclosed system and methods may be embodied in other specific forms without departing from the spirit or essential characteristics thereof. The forgoing implementations are therefore to be considered in all respects illustrative, rather than limiting of the invention.

CONCLUSION

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

What is claimed:

1. A method for selecting optical coherence tomography (OCT) images, the method comprising:
   receiving a plurality of optical coherence tomography (OCT) images;
   for each of the plurality of OCT images:
     identifying a boundary line between a first set of retina pixels and a second set of non-retina pixels in the respective OCT image;
     calculating a derivative of the boundary line between the first set of retina pixels and the second set of non-retina pixels in the respective OCT image;
   selecting an OCT image from the plurality of OCT images as containing a fovea by identifying the OCT image having the derivative of the boundary line between the first set of retina pixels and the second set of non-retina pixels with a greatest magnitude; and
   determining at least one feature of the retina tissue based on the selected OCT image.

2. The method of claim 1, further comprising discarding a portion of the plurality of OCT images prior to identifying the boundary line between the first set of retina pixels and the second set of non-retina pixels.

3. The method of claim 1, wherein the derivative of the boundary line between the first set of retina pixels and the second set of non-retina pixels is a second derivative of the boundary line between the first set of retina pixels and the second set of non-retina pixels.

4. The method of claim 1, further comprising determining if the derivative of the boundary line between the first set of retina pixels and the second set of non-retina pixels crosses a predetermined threshold.

5. The method of claim 1, further comprises receiving a prior probability distribution for the boundary line between the first set of retina pixels and the second set of non-retina pixels.

6. The method of claim 1, further comprising calculating a probability that each point of the boundary line between the first set of retina pixels and the second set of non-retina pixels corresponds to a fovea.

7. The method of claim 6, wherein the probability is calculated using Bayes' rule.

8. The method of claim 1, further comprising identifying the boundary line between the first set of retina pixels and the second set of non-retina pixels in the respective OCT image using a Bayesian level set algorithm to classify each pixel of the respective OCT image as a retina or a non-retina pixel.

9. The method of claim 8, wherein the boundary line between the first set of retina pixels and the second set of non-retina pixels is a substantially shortest path between the retina and the non-retina pixels.

10. The method of claim 1, further comprising applying a smoothing filter to the derivative of the boundary line between the first set of retina pixels and the second set of non-retina pixels.

11. A system for selecting clinically relevant optical coherence tomography (OCT) images, the system comprising a memory and one or more processors configured to execute instructions stored in the memory, execution of the instructions cause the one or more processors to:
  receive a plurality of optical coherence tomography (OCT) images;
  for each of the plurality of OCT images:
    identify boundary line between the first set of retina pixels and the second set of non-retina pixels in the respective OCT image;
    calculate a derivative of the boundary line between the first set of retina pixels and the second set of non-retina pixels in the respective OCT image;
  select an OCT image from the plurality of OCT images as containing a fovea by identifying the OCT image having the derivative of the boundary line between the first set of retina pixels and the second set of non-retina pixels in the respective OCT image with a greatest magnitude; and
  determine at least one feature of the retina tissue based on the selected OCT image.

12. The system of claim 11, wherein the instructions cause the one or more processors to discard a portion of the plurality of OCT images prior to identifying the boundary line between the first set of retina pixels and the second set of non-retina pixels.

13. The system of claim 11, wherein the derivative of the boundary line between the first set of retina pixels and the second set of non-retina pixels is a second derivative of the boundary line between the first set of retina pixels and the second set of non-retina pixels.

14. The system of claim 11, wherein the instructions cause the one or more processors to determine if the derivative of the boundary line between the first set of retina pixels and the second set of non-retina pixels crosses a predetermined threshold.

15. The system of claim 11, wherein the instructions cause the one or more processors to receive a prior probability distribution for the boundary line between the first set of retina pixels and the second set of non-retina pixels in the respective OCT image.

16. The system of claim 11, wherein the instructions cause the one or more processors to calculate a probability that each point of the boundary line between the first set of retina pixels and the second set of non-retina pixels corresponds to a fovea.

17. The system of claim 16, wherein the probability is calculated using Bayes' rule.

18. The system of claim 11, wherein the instructions cause the one or more processors to identify the boundary line between the first set of retina pixels and the second set of non-retina pixels in the respective OCT image using a Bayesian level set algorithm to classify each pixel of the respective OCT image as a retina or a non-retina pixel.

19. The system of claim 18, wherein the boundary line between the first set of retina pixels and the second set of non-retina pixels is a substantially shortest path between the retina and the non-retina pixels.

20. The system of claim 11, wherein the instructions cause the one or more processors to apply a smoothing filter to the derivative of the boundary line between the first set of retina pixels and the second set of non-retina pixels.

* * * * *